(12) United States Patent
Adkins et al.

(10) Patent No.: US 7,150,720 B2
(45) Date of Patent: Dec. 19, 2006

(54) FOOT MASSAGING DEVICE WHICH PROVIDES RELIEF TO VARIOUS BODY PARTS THROUGH REFLEXOLOGY AND METHOD THEREFOR

(76) Inventors: Victor J. Adkins, 8337 Valley Stream Ave., Las Vegas, NV (US) 89131; Chikae Adkins, 8337 Valley Stream Ave., Las Vegas, NV (US) 89131

(*) Notice: Subject to any disclaimer, the term of this patent is extended or adjusted under 35 U.S.C. 154(b) by 263 days.

(21) Appl. No.: 10/910,085

(22) Filed: Aug. 3, 2004

(65) Prior Publication Data
US 2006/0030799 A1   Feb. 9, 2006

(51) Int. Cl.
*A61H 9/00* (2006.01)
(52) U.S. Cl. ............... 601/22; 601/28; 601/104; 601/134; 601/148
(58) Field of Classification Search ............ 601/19, 601/22, 27, 28, 35, 104, 105, 133, 134, 148–151, 601/157; 4/622; 602/13, 23, 27–29
See application file for complete search history.

(56) References Cited

U.S. PATENT DOCUMENTS

| | | | | | |
|---|---|---|---|---|---|
| 3,283,756 | A | * | 11/1966 | Turley | 601/166 |
| 3,837,334 | A | * | 9/1974 | Johnson | 601/19 |
| 4,513,736 | A | * | 4/1985 | Thurber | 601/57 |
| 4,620,529 | A | * | 11/1986 | Kurosawa | 601/157 |
| 6,405,390 | B1 | * | 6/2002 | Kuen | 4/622 |
| 6,602,212 | B1 | * | 8/2003 | Ahn | 601/27 |

* cited by examiner

*Primary Examiner*—Quang D. Thanh
(74) *Attorney, Agent, or Firm*—Jeffrey D. Moy; Harry M. Weiss; Weiss & Moy, P.C.

(57) ABSTRACT

A foot massaging device has a body section. A pair of foot holding devices are coupled to an interior of the body section. The foot holding device has an elongated housing for holding a foot and an opening located at a top section of the elongated housing for inserting the foot into the elongated housing. At least one massaging device is coupled to an interior section of the elongated housing for massaging the foot and for applying pressure to certain areas of the foot to relieve body aches based on reflexology.

20 Claims, 4 Drawing Sheets

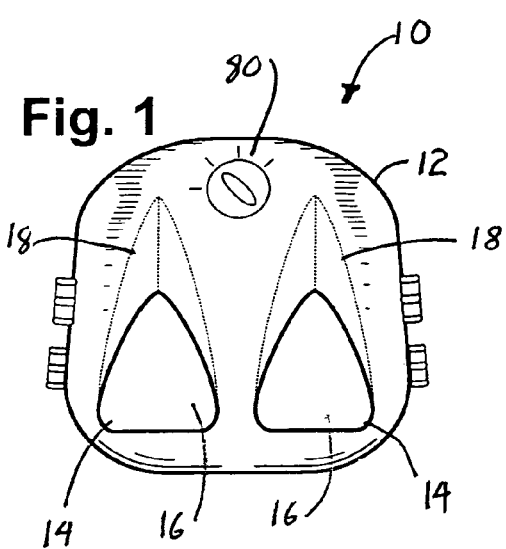
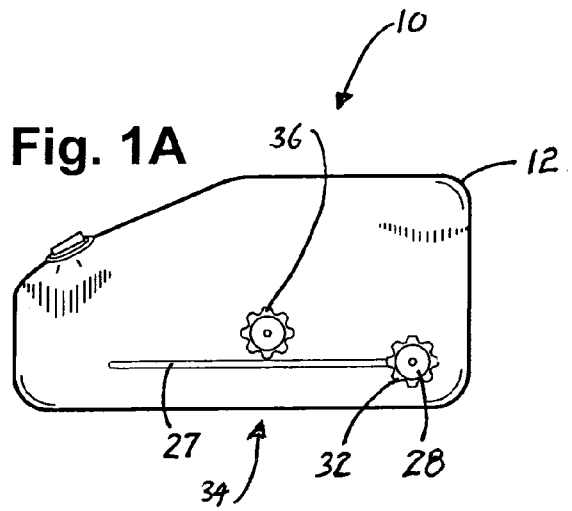
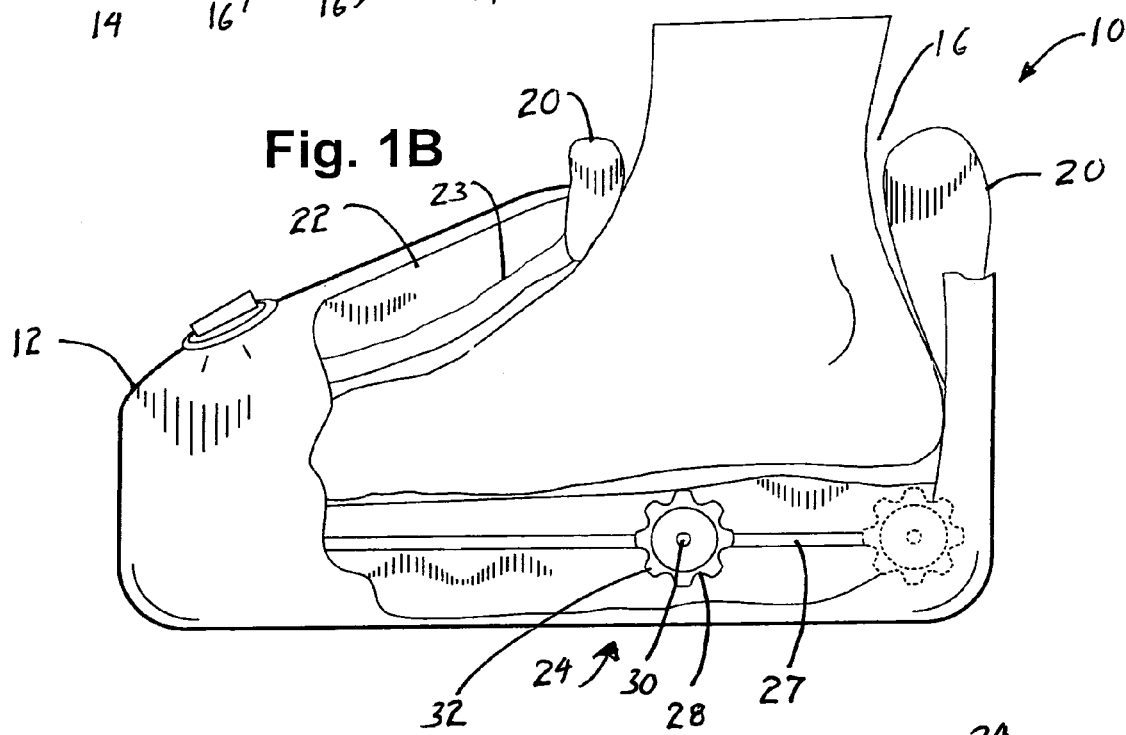
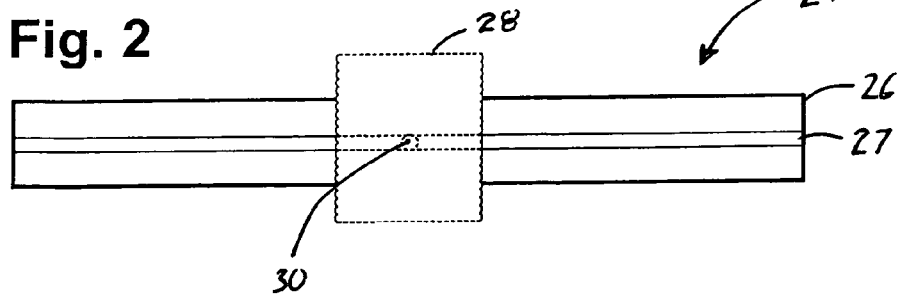

FOOT MASSAGING DEVICE WHICH PROVIDES RELIEF TO VARIOUS BODY PARTS THROUGH REFLEXOLOGY AND METHOD THEREFOR

BACKGROUND OF THE INVENTION

1. Field of the Invention

This invention relates to foot massager and, more specifically, to a device for massaging the feet of a person and which provides relief to other body parts through the concept of reflexology.

2. Description of the Prior Art

Foot massaging devices are well known in the prior art. In general, most foot massaging devices use a vibrational mechanism to massage the bottom of one's foot. Unfortunately, present foot massaging devices have not been very satisfactory. These prior art foot massaging devices do not provide an effective massaging pattern to make them beneficial to fully provide a soothing and relaxing effect.

Another problem with prior art foot massaging devices is that current foot massaging devices only massage and provide relief to the bottom of one's foot. The concept of reflexology involves the relief of stress in various parts of the human body by vigorous stimulation of specific areas located on the sole of the foot. For example, the area of the big toe is associated with relieving sinus problems. The area at the ball of the foot is associated with stomach disorders. Each specific area of the sole of the foot is connected to a different organ of the body according to those who practice reflexology. Present foot massaging devices do not give an adequately deep tissue massage to all the specific reflexology points of the sole of a users foot.

Therefore, there is a need to provide an improved foot massaging device. The improved foot massaging device must overcome the problem associated with prior art foot massaging devices. The improved foot massaging device must be able to provide relief to other body parts through the concept of reflexology.

SUMMARY OF THE INVENTION

In accordance with one embodiment of the present invention, it is an object of the present invention to provide an improved foot massaging device.

It is another object of the present invention to provide an improved foot massaging device that overcomes the problem associated with prior art foot massaging devices.

It is still another object of the present invention to provide an improved foot massaging device that is able to provide relief to other body parts through the concept of reflexology.

BRIEF DESCRIPTION OF THE EMBODIMENTS

In accordance with one embodiment of the present invention a foot massaging device is disclosed. The foot massaging device has a body section. A pair of foot holding devices are coupled to an interior of the body section. The foot holding device has an elongated housing for holding a foot and an opening located at a top section of the elongated housing for inserting the foot into the elongated housing. At least one massaging device is coupled to an interior section of the elongated housing for massaging the foot and for applying pressure to certain areas of the foot to relieve body aches based on reflexology.

In accordance with another embodiment of the present invention a foot massaging device is disclosed. The foot massaging device has a body section. A pair of foot holding devices are coupled to an interior of the body section. The foot holding device has an elongated housing for holding a foot and an opening located at a top section of the elongated housing for inserting the foot into the elongated housing. At least one massaging device is coupled to an interior section of the elongated housing for massaging the foot and for applying pressure to certain areas of the foot to relieve body aches based on reflexology. One massaging device is an air bladder coupled to a top interior section of the elongated housing. Air is inserted into the air bladder to expand the air bladder to keep the foot in the foot holding device. Air may further be inserted and released from the air bladder to expand and contract the air bladder to massage a top area of the foot. A roller massaging device is coupled to a bottom section of the elongated housing. The roller massaging device massages a bottom section of the foot. The roller massaging device can apply pressure to certain areas of the foot to relieve body aches based on reflexology. A heel massaging device is coupled to an interior section of the elongated housing for massaging a heel of the foot.

The foregoing and other objects, features, and advantages of the invention will be apparent from the following, more particular, description of the preferred embodiments of the invention, as illustrated in the accompanying drawing.

BRIEF DESCRIPTION OF THE DRAWINGS

The novel features believed characteristic of the invention are set forth in the appended claims. The invention itself, as well as a preferred mode of use, and advantages thereof, will best be understood by reference to the following detailed description of illustrated embodiments when read in conjunction with the accompanying drawings.

FIG. 1 is a top view of the foot massaging device of the present invention.

FIG. 1A is a side view of the foot massaging device depicted in FIG. 1 with a rolling foot massager mechanism.

FIG. 1B is a close-up cut away side view of the foot massaging device depicted in FIG. 1A in use.

FIG. 2 is a cross sectional view of the rolling foot massager mechanism used in the foot massaging device of the present invention.

DETAILED DESCRIPTION OF THE PREFERRED EMBODIMENT

Figure 3:
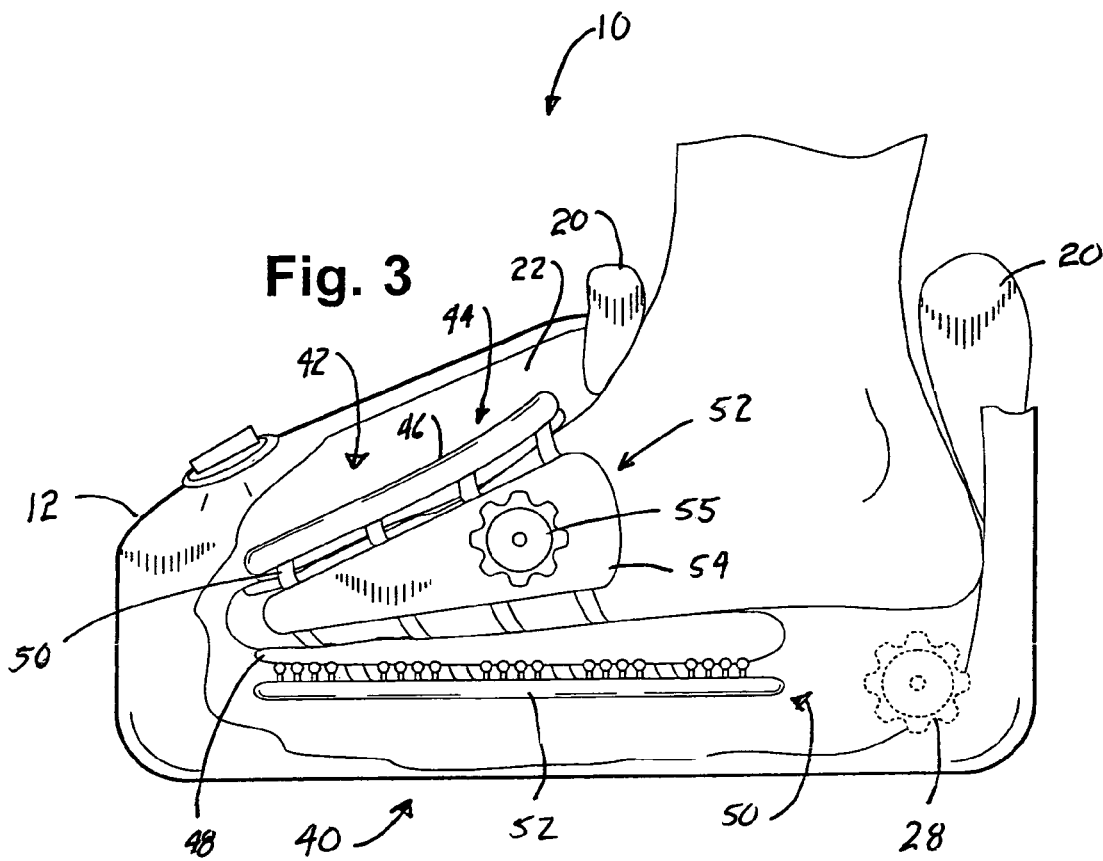
FIG. 3 is a side view of the foot massaging device depicted in FIG. 1 with a second foot massager mechanism installed.
Figure 3A:
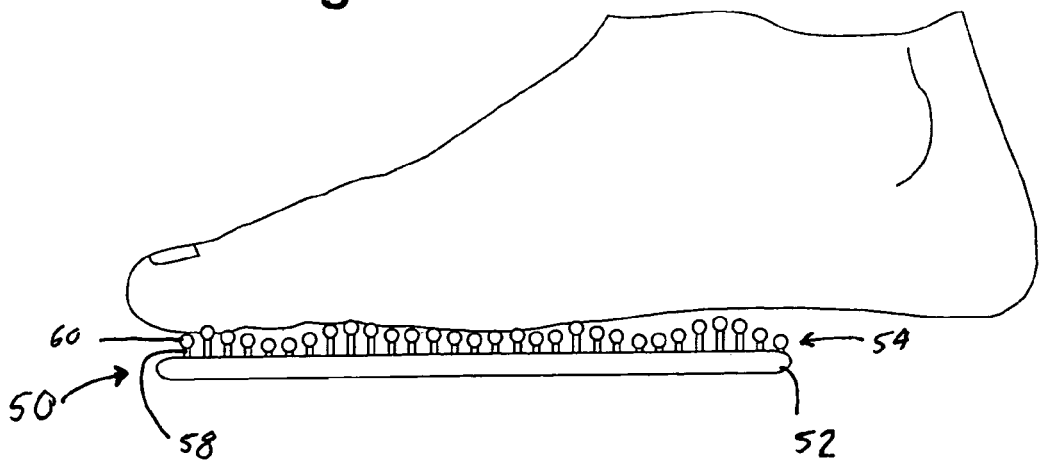
FIG. 3A is a side view of a bottom foot massaging section of the second foot massager mechanism used in the foot massaging device depicted in FIG. 3.

Referring to FIGS. 1–1B, a foot massaging device 10 of the present invention is shown. The foot massaging device 10 massages the foot and uses the concept of reflexology to provide relief to the foot and other body parts of a user.

The foot massaging device 10 has a body section 12. The body section 12 is made out of a light weight but sturdy material. For example, plastic or a lightweight metal like aluminum or tin may be used. The above are given as an example and should not be seen as to limit the scope of the present invention.

The body section 12 houses a pair of foot holders 14. The foot holders 14 are used to hold the user's feet in place in the foot massaging device 10 while the user receives a foot massage. The foot holder 14 is shaped similar to a high-top shoe having an opening 16 and an elongated body section 18. Padding 20 is placed around the opening 16. The padding 20 is used to provide a comfortable surrounding to the ankle region of the user when a user inserts his foot into a foot holder 14. The padding 20 will prevent chaffing around the ankle region of the user.

Located internal to the body section 18 is an air bladder 22. The air bladder 22 is similar to that used when one has his blood pressure taken. The air bladder 22 can function in two different manners. First, the air bladder 22 may be used to massage the foot. The air bladder 22 may continuously expand and contract by automatically inflating and deflating to apply gentle pressure to the top of the foot. This gentle pressure will massage the foot thereby increasing blood circulation to the foot. Secondly, the air bladder may be used to secure the foot of the user in the foot holder 14. Once a foot is inserted into the foot holder 14, one can inflate the air bladder 22 to secure the foot in the foot holder 14. The air bladder 22 is deflated to allow one to remove the foot from the foot holder 14.

The air bladder 22 may be a heated air bladder 22. A plurality of heating lines 23 may be placed on the surface of the air bladder 22 closest to the top of the foot. The heating lines 23 would be similar to those found in a heating blanket. The heating lines 23 would be used to warm up and relax the muscles in the foot thereby further aiding in the massaging process.

Located on the bottom of the elongated body section 18 is a roller massage device 24. The roller massage device 24 is used to massage the bottom of ones foot and to apply pressure to certain portions of the bottom of the foot. The roller massage device 24 has a track member 26. The track member 26 extends along a majority of the length of the elongated body section 18. In a central area of the track member 26 is a channeling 27. A roller massager 28 is positioned in the channeling 27. The roller massager 28 will rotate about an axle 30 and travel up and down the track member 26 via the channeling 27. The roller massage 28 may continuously move up and down the track member 26 thereby massaging the bottom of the foot. Alternatively, the roller massage 28 may be locked into a certain position. When locked in a desired position, the roller massage 28 will continue to rotate, thereby massaging the desired location.

The roller massager 28 has a plurality of raised members 32 extend up from the roller massager 28. The raised members 32 will apply gentle pressure to the bottom of one's foot thereby massaging the foot. The raised members 32 may also apply pressure to certain areas of the foot. The pressure to certain points on the foot will relieve certain body ailments as practiced in the science of reflexology.

A locking device 34 is coupled to the roller massage device 24. The locking device 34 is used to lock the roller massage device 24 in a desired location. The locking device 34 will have a handle 36 located on the outside of the body section 12. The handle 36 is coupled to the roller massage device 24 so that by rotating the handle 36, one locks the roller massage device 24 in a desired position. When one loosens the handle 36, the roller massager 28 will be free to continuously move up and down the track 26 thereby massaging the bottom of the foot.

Figure 4:
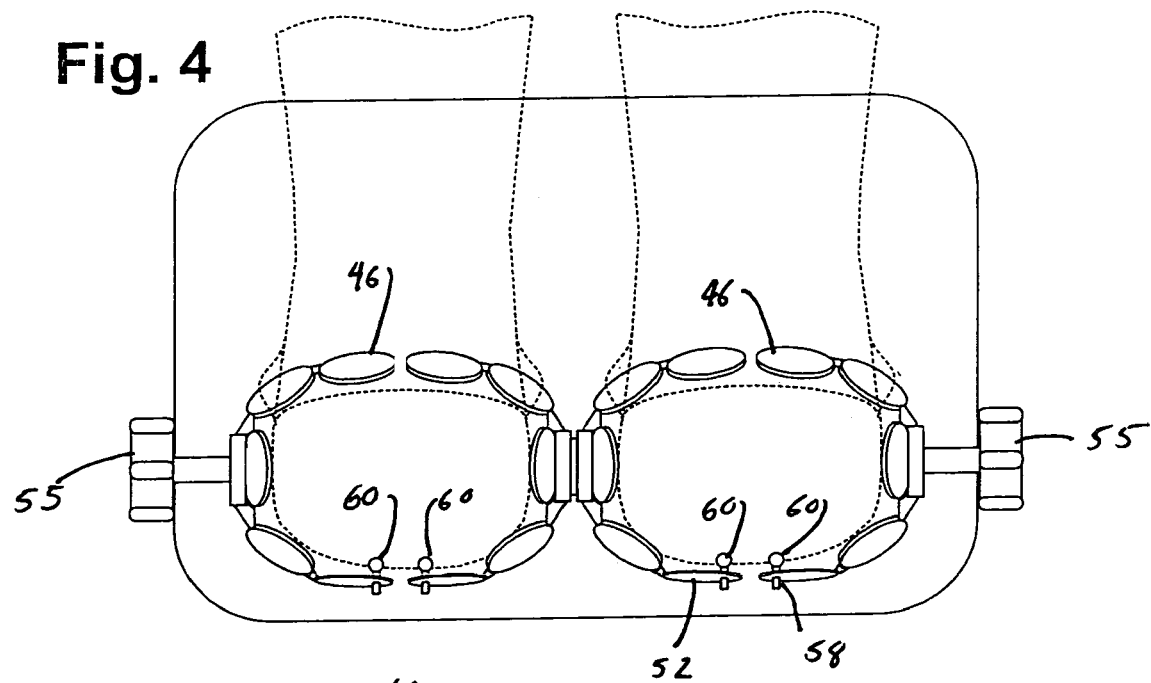
FIG. 4 is a rear view of the foot massaging device depicted in FIG. 3.
Figure 4A:
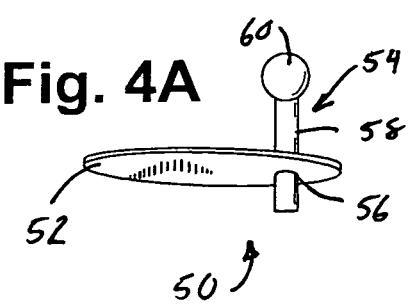
FIG. 4A is a side view of one embodiment of the magnetized pins used in the foot massaging device depicted in FIG. 3.
Figure 4B:
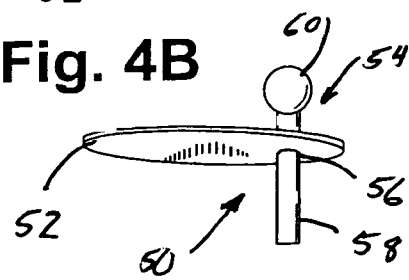
FIG. 4B is a side view of another embodiment of the magnetized pins used in the foot massaging device depicted in FIG. 3.

Referring now to FIGS. 3–4B, a second massaging device 40 is shown. The second massaging device 40 is also be inserted into each foot holder 14. The second massaging device 40 may be placed directly on top of the roller massage device 24 with the roller massager 28 pushed back to the rear of the foot holder 14. Alternatively, the roller massager 28 may be removed and the second massaging device 40 inserted into each foot holder 14.

The second massaging device 40 has a foot holding mechanism 42. The foot holding mechanism 42 has a body section 44. The body section 44 is conical in shape having a first opening which allows a foot to be inserted and a second opening to allow the toes of the foot to exit. The body section 44 may be sized so that the entire foot is held in the body section 44 or only a portion of the foot is held.

The body section 44 has a top member 46 and a bottom member 48. Both the top and bottom sections 46 and 48 are padded to provide additional comfort to the user. The top and bottom sections 46 and 48 are coupled together by a plurality of strap members 50. A tightening device 52 is coupled to each of the strap members 50. The tightening device 52 will allow one to lower the top section 46 so as to hold the foot of the user comfortably in the body section 44.

In the embodiment depicted in FIG. 3, the tightening device 52 has a body member 54. The strap members 50 are coupled to a top and bottom surface of the body member 54. A knob 55 is coupled to the body member 54. By rotating the knob 55, one may tighten the body section 44. This is accomplished by pulling the strap members 50 closer together. By rotating the knob 55 in the opposite direction, one may loosen the body section 44 by pushing the strap members 50 apart. The pressure to certain points on the foot will relieve certain body ailments as practiced in the science of reflexology.

Located below the bottom section 48 is a pressure massager 50. The pressure massager 50 applies pressure to the bottom of the foot to massager the foot. Furthermore, as discussed above, applying pressure to certain points on the foot will relieve certain body ailments as practiced in the science of reflexology.

The pressure massager 50 is comprised of a pad 52. The pad 52 generally runs the length of the user's foot. A plurality of magnetized pressure pins 54 are coupled to the pad 52. Magnetized pressure pins 54 are used as a form of magnet therapy. Magnet therapy, or magnetic therapy, is a form of alternative medicine based on the concept that certain medical disorders can be effectively treated by exposure to magnetic fields. Some believe that magnetic fields emanating from permanent magnets placed close to the body can cause bones to heal faster, relieve pain, and perform other forms of healing to the body. Thus, the magnetic fields emanating from magnetized pressure pins 54 can aid in healing the body.

The plurality of magnetized pressure pins 54 are coupled to the pad 52 in a manner that allows each of the magnetized pressure pins 54 to be automatically raised and lowered by the pressure being applied. Thus, magnetized pressure pins 54 of the pressure massager 50 are designed to conform to the shape of the foot.

Figure 3B:
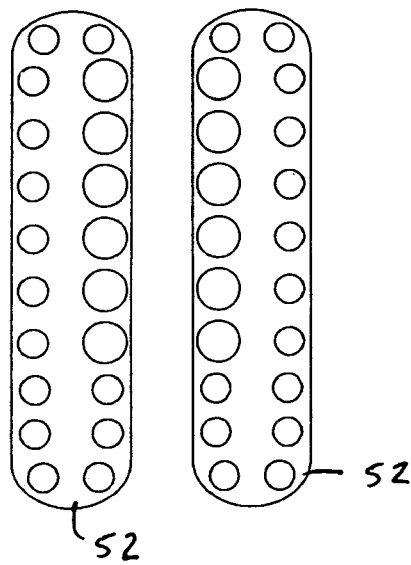
FIG. 3B is a top view of one embodiment of the bottom foot massaging section depicted in FIG. 3A.
Figure 3C:
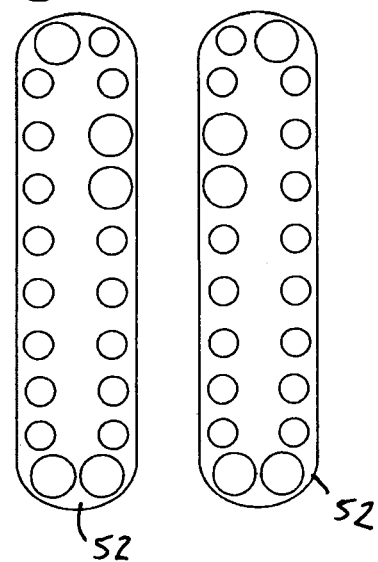
FIG. 3C is a top view of another embodiment of the bottom foot massaging section depicted in FIG. 3A.

As shown more clearly in FIGS. 4A and 4B, the pad 52 will have a plurality of openings 56. Each magnetized pressure pin 54 has a shaft 58 which is inserted through the opening 56. A spherical top 60 is placed on the top of the shaft 58. The size of the spherical top 60 will vary. As shown in FIGS. 3B and 3C, different size spherical tops 60 can be placed at different locations to provide certain pressure to the foot. For example, bigger size spherical tops 60 may be positioned to target the arch of the foot. However, this is only given as an example and should not be seen as to limit the scope of the present invention. Furthermore, as shown in FIGS. 3B and 3C, a channeling runs down the center of the 52. The channeling is used so that the roller massager 28 can be used in combination with the pressure massager 50.

Figure 5:
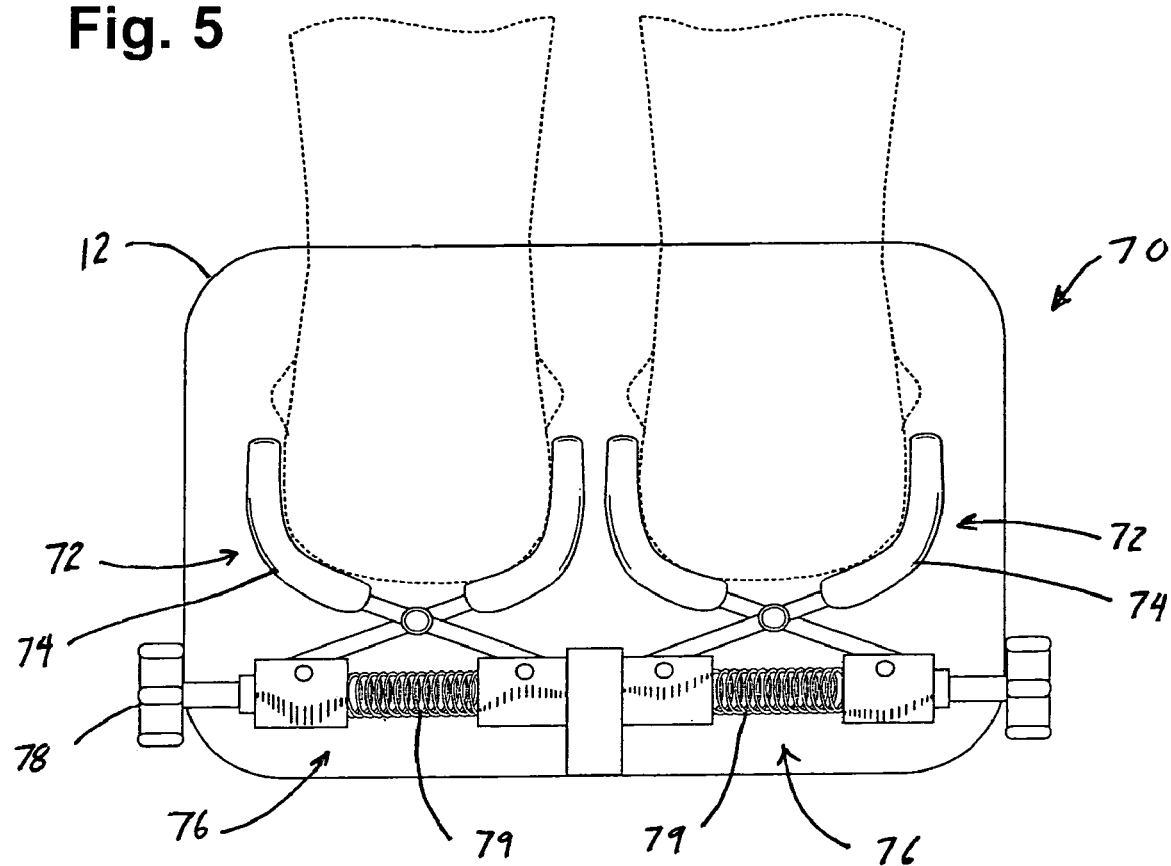
FIG. 5 is a rear view of the foot massing device depicted in FIG. 1 with a third foot massager mechanism.
Figure 5A:
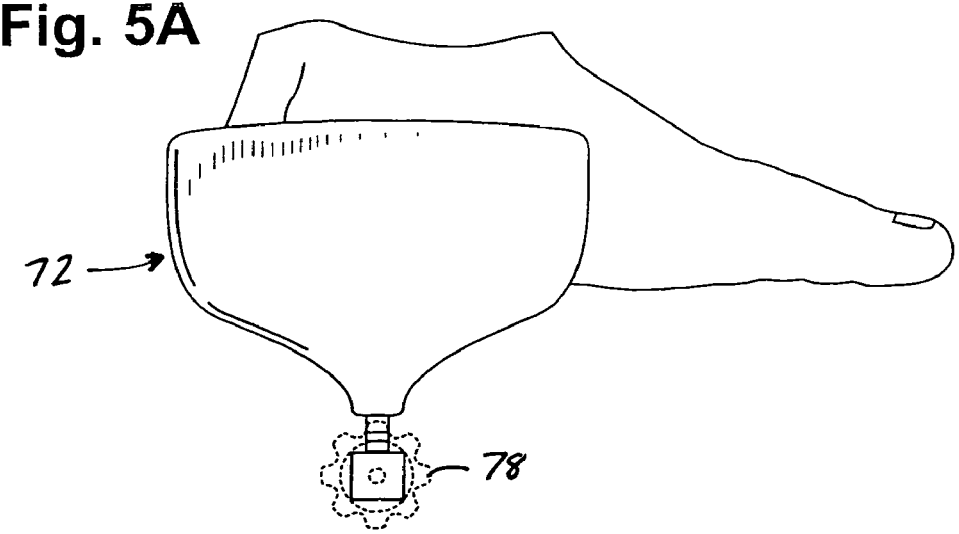
FIG. 5A is a side view of the third foot massager mechanism.

Referring now to FIGS. 5–5A, a heel massaging device 70 is shown. The heel massaging device 70 applies pressure to the heel of the foot in order to massage the heel and provide relief to the heel and other body parts through the science of reflexology.

The heel massaging device 70 is comprised of a cradle section 72. The cradle section 72 is used to hold the heel of the foot of the user. The cradle section 72 is comprised of a pair of arm members 74. The arm members 72 have a top section which is slightly rounded to conform to the shape of the heel. The top section of the arm members 72 are generally padded so as to provide additional comfort to the user.

The arm members 72 are coupled at a bottom section to a tightening device 76. The tightening device 76 is used to adjust the amount of pressure the arm members 72 exert on the heel. The tightening device 76 has a spring member 79 coupled to the bottom section of both arm members 72. A handle 78 is also coupled to the bottom section of the arm member 72 and to the spring member 79. The handle 78 is used to tighten the spring 79, thereby closing the arm members 72. Closing the arm members 72 will increase the pressure applied to the heel of the user in order to massage the heel and provide relief to the heel and other body parts through the science of reflexology.

The air bladder 22, the roller massage device 24, the second massaging device, and the heel massaging device 70 may all be placed in the foot holders 14 individually or all together. The air bladder 22 and the roller massage device 24 may be coupled to a power supply for running these devices. The power supply may be a battery pack, a power outlet, or the like. If all of the different massaging devices are installed, a selection switch 80 is coupled to the body section 12. The selection switch 80 is further coupled to each of the above mentioned devices. By moving the selection switch, one may select which massaging device or devices the user wishes to use. The selection switch 80 may further be a wired or wireless remote control device to activate different massaging devices.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A foot massaging device comprising:
    a body section,
    a pair of foot holding devices coupled to an interior of the body section, the foot holding device having an elongated housing for holding a foot and an opening located at a top section of the elongated housing for inserting the foot into the elongated housing; and
    at least one massaging device coupled to an interior section of the elongated housing for massaging the foot and for applying pressure to certain areas of the foot to relieve body aches based on reflexology, wherein the at least one massaging device comprises:
    a foot pressure massaging device coupled to the interior section of the elongated housing for applying pressure to top and bottom surfaces of the foot; and
    a magnetized pressure pin massager coupled to a bottom interior section of the elongated housing for massaging the bottom of the foot and for applying magnet therapy to the foot.

2. A foot massaging device in accordance with claim 1 wherein the at least one massaging device further comprises:
    an air bladder coupled to a top interior section of the elongated housing, air being inserted into the air bladder to expand the air bladder to keep the foot in the foot holding device, the air may further be inserted and released from the air bladder to expand and contract the air bladder to massage a top area of the foot; and
    a roller massaging device coupled to a bottom section of the elongated housing, the roller massaging device massaging a bottom section of the foot, the roller massaging device applying pressure to certain areas of the foot to relieve body aches based on reflexology.

3. A foot massaging device in accordance with claim 2 wherein the roller massaging device comprises:
    a track which runs a length of the elongated housing;
    a channeling formed in the track; and
    a roller mechanism which moves in the channeling to massage the bottom of the foot, the roller mechanism having a plurality of raised members formed on an outer surface of the roller mechanism, the raised members used for massaging the bottom of the foot and applying pressure to certain areas of the bottom of the foot.

4. A foot massaging device in accordance with claim 2 wherein the roller massaging device comprises a locking device coupled to the roller massaging device for locking the roller massaging device in a set location.

5. A foot massaging device in accordance with claim 1 wherein the foot pressure massaging device comprises:
    a funnel shaped housing having a first opening for inserting the foot and a second opening for allowing toes of the foot to exit, the funnel shaped housing comprising:
    a padded top member;
    a padded bottom member;
    a plurality of straps for coupling the padded top member to the padded bottom member; and
    a tightening device coupled to the plurality of straps for tightening and loosening the foot pressure massaging device.

6. A foot massaging device in accordance with claim 5 wherein the tightening device comprises:
    a body section coupled to the plurality of straps; and
    a knob coupled to the body section for contracting and expanding the plurality of straps to tighten and loosen the foot pressure massaging device.

7. A foot massaging device in accordance with claim 1 wherein the magnetized pressure pin massager comprises:
    a pad coupled to the bottom interior section of the elongated housing wherein the pad has a plurality of holes; and a magnetized pressure pin located in each of the plurality of holes for massaging the bottom of the foot and for applying magnet therapy to the foot.

8. A foot massaging device in accordance with claim 7 wherein the magnetized pressure pin comprises:
- a rod member located in each of the plurality of holes; and
- a magnetized spherical head coupled to the top of the rod member for massaging the bottom of the foot and for applying magnet therapy to the foot.

9. A foot massaging device in accordance with claim 1 wherein the at least one massaging device further comprises a heel massaging device.

10. A foot massaging device in accordance with claim 9 wherein the heel massaging device comprises:
- a cradle device for holding a heel of the foot; and
- a pressure adjusting device coupled to the cradle device for adjusting the pressure applied by the cradle device.

11. A foot massaging device in accordance with claim 10 wherein the cradle device comprises:
- a first arm member having an arched top member, wherein the arched top member is padded; and
- a second arm member coupled to the first arm member wherein the second arm member has an arched top member, wherein the arched top member is padded.

12. A foot massaging device in accordance with claim 11 wherein the pressure adjusting device comprises:
- a spring mechanism coupled to a bottom section of the first arm member and the second arm member; and
- a knob coupled to the spring mechanism to tighten and loosen the spring mechanism for adjusting the pressure applied by the cradle device.

13. A foot massaging device comprising:
- a body section,
- a pair of foot holding devices coupled to an interior of the body section, the foot holding device having an elongated housing for holding a foot and an opening located at a top section of the elongated housing for inserting the foot into the elongated housing; and
- at least one massaging device coupled to an interior section of the elongated housing for massaging the foot and for applying pressure to certain areas of the foot to relieve body aches based on reflexology, wherein the at least one massaging device comprises:
  - an air bladder coupled to a top interior section of the elongated housing, air being inserted into the air bladder to expand the air bladder to keep the foot in the foot holding device, the air may further be inserted and released from the air bladder to expand and contract the air bladder to massage a top area of the foot;
  - a roller massaging device coupled to a bottom section of the elongated housing, the roller massaging device massaging a bottom section of the foot, the roller massaging device applying pressure to certain areas of the foot to relieve body aches based on reflexology; and
  - a heel massaging device coupled to an interior section of the elongated housing for massaging a heel of the foot.

14. A foot massaging device in accordance with claim 13 wherein the at least one massaging device further comprises:
- a foot pressure massaging device coupled to the interior section of the elongated housing for applying pressure to top and bottom surfaces of the foot; and
- a magnetized pressure pin massager coupled to a bottom interior section of the elongated housing for massaging the bottom of the foot and for applying magnet therapy to the foot.

15. A foot massaging device in accordance with claim 14 wherein the foot pressure massaging device comprises:
- a funnel shaped housing having a first opening for inserting the foot and a second opening for allowing toes of the foot to exit, the funnel shaped housing comprising:
- a padded top member;
- a padded bottom member;
- a plurality of straps for coupling the padded top member to the padded bottom member; and
- a tightening device coupled to the plurality of straps for tightening and loosening the foot pressure massaging device, the tightening device comprises:
- a body section coupled to the plurality of straps; and
- a knob coupled to the body section for contracting and expanding the plurality of straps to tighten and loosen the foot pressure massaging device.

16. A foot massaging device in accordance with claim 14 wherein the magnetized pressure pin massager comprises:
- a pad coupled to the bottom interior section of the elongated housing wherein the pad has a plurality of holes; and
- a magnetized pressure pin located in each of the plurality of holes for massaging the bottom of the foot and for applying magnet therapy to the foot, wherein the magnetized pressure pin comprises:
- a rod member located in each of the plurality of holes; and
- a magnetized spherical head coupled to the top of the rod member for massaging the bottom of the foot and for applying magnet therapy to the foot.

17. A foot massaging device in accordance with claim 13 wherein the roller massaging device comprises:
- a track which runs a length of the elongated housing;
- a channeling formed in the track;
- a roller mechanism which moves in the channeling to massage the bottom of the foot, the roller mechanism having a plurality of raised members formed on an outer surface of the roller mechanism, the raised members used for massaging the bottom of the foot and applying pressure to certain areas of the bottom of the foot; and
- a locking device coupled to the roller massaging device for locking the roller massaging device in a set location.

18. A foot massaging device in accordance with claim 13 wherein the heel massaging device comprises:
- a cradle device for holding a heel of the foot; and
- a pressure adjusting device coupled to the cradle device for adjusting the pressure applied by the cradle device.

19. A foot massaging device in accordance with claim 18 wherein the cradle device comprises:
- a first arm member having an arched top member, wherein the arched top member is padded; and
- a second arm member coupled to the first arm member wherein the second arm member has an arched top member, wherein the arched top member is padded.

20. A foot massaging device in accordance with claim 19 wherein the pressure adjusting device comprises:
- a spring mechanism coupled to a bottom section of the first arm member and the second arm member; and
- a knob coupled to the spring mechanism to tighten and loosen the spring mechanism for adjusting the pressure applied by the cradle device.

\* \* \* \* \*